(12) United States Patent
Nishida et al.

(10) Patent No.: US 7,189,407 B2
(45) Date of Patent: Mar. 13, 2007

(54) COMPOSITION FOR EXTERNAL USE

(75) Inventors: Miharu Nishida, Yokohama (JP); Masaaki Ishiwatari, Yokohama (JP)

(73) Assignee: Shiseido Co., Ltd., Tokyo (JP)

( * ) Notice: Subject to any disclaimer, the term of this patent is extended or adjusted under 35 U.S.C. 154(b) by 205 days.

(21) Appl. No.: 10/408,289

(22) Filed: Apr. 8, 2003

(65) Prior Publication Data

US 2003/0211067 A1    Nov. 13, 2003

Related U.S. Application Data

(60) Continuation of application No. 09/986,120, filed on Nov. 7, 2001, now abandoned, which is a division of application No. 09/400,535, filed on Sep. 21, 1999, now abandoned.

(30) Foreign Application Priority Data

Sep. 21, 1998    (JP)    ................... 10-284784

(51) Int. Cl.
*A61K 6/00*    (2006.01)
*A61K 8/02*    (2006.01)
*A61K 33/00*    (2006.01)
*A61K 31/715*    (2006.01)

(52) U.S. Cl. .............. 424/401; 424/600; 514/54; 514/770; 514/844

(58) Field of Classification Search ............. 424/401, 424/600; 514/54, 770, 844
See application file for complete search history.

(56) References Cited

U.S. PATENT DOCUMENTS 4,174,386 A  *  11/1979  Spitzer et al. ................ 424/47
5,165,915 A     11/1992  Tokubo et al.
5,466,283 A     11/1995  Kondo et al.
5,484,816 A      1/1996  Yanagida et al.
5,827,920 A     10/1998  Watanabe et al.
6,008,246 A     12/1999  Ito et al.
6,036,730 A      3/2000  Yoshida et al.
6,074,652 A      6/2000  Ishiwatari et al.
6,077,520 A      6/2000  Tominaga
6,228,378 B1 *   5/2001  Takanabe et al. .......... 424/401

FOREIGN PATENT DOCUMENTS

| EP | 0 838 212 A1 | 4/1998 |
| EP | 0 894 491 | 7/1998 |
| EP | 0 277 244 | 8/1998 |
| JP | 05192560 A * | 8/1993 |
| JP | 6-74283 | 9/1994 |
| JP | 7-258055 | 10/1995 |
| JP | 8-208434 | 8/1996 |
| JP | 9-175924 | 7/1997 |
| JP | 9-227338 | 9/1997 |
| JP | 9-241115 | 9/1997 |
| WO | WO 97/49376 | 12/1997 |
| WO | WO 98/31330 | 7/1998 |

OTHER PUBLICATIONS

Lewis, Richard. Sr., *Hawley's Condensed Chemical Dictionary*, p. 277, New York: Van Nostrand Reinhold, 1997.

* cited by examiner

*Primary Examiner*—Sreeni Padmanabhan
*Assistant Examiner*—Marina Lamm
(74) *Attorney, Agent, or Firm*—Snider & Associates; Ronald R. Snider

(57) ABSTRACT

A compositions for external use comprising succinoglucan and a water-swelling clay mineral, which is useful particularly as cosmetics. The composition can give a novel feeling upon use which satisfies the diversified requirements by consumers and is excellent in long-term stability.

12 Claims, No Drawings

COMPOSITION FOR EXTERNAL USE

RELATED APPLICATIONS

This application is a continuation of U.S. application Ser. No. 09/986,120, filed Nov. 7, 2001 now abandoned, which was a continuation of U.S. application Ser. No. 09/400,535 filed Sep. 21, 1999 now abandoned. This application claims the priority of Japanese Patent Application No. 10-284784, filed on Sep. 21, 1998, which is incorporated herein by reference.

FIELD OF THE INVENTION

This invention falls within the category of the technical field relating to a composition for external uses. More particularly, it relates to a composition for external use which is excellent in the feeling upon use, has a long-term stability, and is useful particularly as cosmetics.

BACKGROUND OF THE INVENTION

In recent years, people, in particular, young people have a preference for cosmetics which make the skin moist and soft and impart a refreshing feeling upon use. This tendency affects not only skin-care products but body-care products and makeup products.

To achieve the above-described feeling upon use, these products generally contain carboxyvinyl polymer as a thickener and stabilizer. However, in the case of products containing compounds which are liable to ionize (for example, ascorbic acid, magnesium phosphate, arginine hydrochloride) or makeup products containing pigments, the thickening effect of carboxyvinyl polymer is seriously inhibited by the ionizable compounds or the pigments. As a result, there arise some problems such as a decrease in viscosity, separation or sedimentation during storage, which makes these products disadvantageous in the long-term stability.

To solve these problems, thickeners such as xanthan gum and hydroxyethylcellulose are employed in some cases. Although a satisfactory long-term stability can be achieved by using these thickeners, there arises another problem of a slimy or sticky feel.

Under these circumstances, the existing products are not much different from each other in the feeling upon use and in the form and, therefore, not always satisfy the diversified requirements by consumers.

Accordingly, an object of the present invention is to provide a composition for external use (e.g., cosmetics, etc.) which can impart a novel feeling upon use to thereby satisfy the diversified requirements by consumers and has a good long-term stability.

SUMMARY OF THE INVENTION

To solve the above-described problems, the present inventors have conducted extensive studies. As a result, they have successfully found that a composition for external use being useful, in particular, as a cosmetic which exhibits a novel feeling upon use (imparting a moist feel, being highly compatible with the skin, giving a extremely refreshing feel, etc.) different from the existing cosmetics and remains stable over a long time without suffering from a decrease in the viscosity, separation or sedimentation can be obtained by using succinoglucan and a water-swelling clay mineral as a substitute for carboxyvinyl polymer for thickening and stabilization, thereby completing the present invention.

Accordingly, the present invention provides a composition for external use comprising succinoglucan and a water-swelling clay mineral.

A composition for external use exhibiting a further preferable feeling upon use can be obtained by further adding an oily component to the above-described composition. Moreover, the desired effects of the present invention can be effectively achieved by adding a surfactant, an alkyl acrylate.methacrylate copolymer to the composition, in particular, that comprising an oily component.

The present invention will be further described below.

The composition for external use according to the present invention (hereinafter, simply referred to as "the composition of the present invention") comprises succinoglucan and a water-swelling clay mineral.

The succinoglucan to be used in the composition of the present invention is a polysaccharide originating in a microorganism. Namely, it means a polysaccharide originating in a microorganism which comprises saccharide units derived from galactose and glucose together with acid units derived from succinic acid, pyruvic acid and, as an optional component, acetic acid, or salts of these acids.

More particularly, succinoglucan is a water-soluble polymer consisting of galactose unit, glucose unit, succinic acid unit and pyruvic acid unit (molar ratio: 1:7:0.8:1) optionally together with acetic acid unit, having a weight average molecular weight of preferably about 6,000,000 or more (more preferably from about 6,000,000 to about 15,000,000), which is represented by the following structural formula.

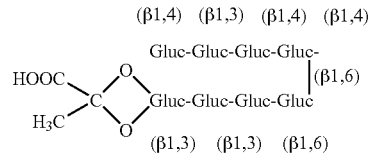

In the above formula, each Gluc represents a glucose unit while each Galac represents a galactose unit. The bonding manner between saccharide units are designated in parentheses. For example, (β1,4) stands for a β1-4 bond.

Examples of the microorganism from which the succinoglucan originates include those belonging to the genera *Pseudomonas*, *Rhizobium*, *Alcaligenes* and *Agrobacterium*. Among all, *Agrobacterium tumefaciens* I-736, which has been deposited with Collection Nationale de Cultures de Microorganism (CNCM) on Mar. 1, 1988 under Budapest treaty and is publicly available under the accession number I-736, belonging to the genus *Agrobacterium* is particularly preferable.

Succinoglucan can be produced by culturing such a microorganism in a medium.

More particularly, succinoglucan can be produced by culturing the microorganism in a medium containing, in general, a carbon source (e.g., glucose, sucrose, starch hydrolyzate, etc.), an organic nitrogen source (e.g., casein, caseinate, vegetable powder, yeast extract, corn steep liquor (CSL), etc.) and inorganic salts (e.g., metal sulfate, metal phosphate, metal carbonate, etc.), optionally together with trace elements.

It is generally preferable to culture the microorganism under a pressure of 1 to 4 bar at a temperature of 25 to 35°

C. under aerobic conditions, for example, with agitation. The pH value of the medium ranges from 5 to 9, preferably from 6 to 8.

After the completion of the culture, the medium may be heated and then brought into contact continuously with an organic solvent such as isopropyl alcohol to precipitate succinoglucan. In order to isolate the succinoglucan from the culture medium, it is preferable to collect the succinoglucan by filtration followed by centrifugation and drying under elevated pressure to give the succinoglucan usable in the composition of the present invention.

Needless to say, the succinoglucan thus produced can be employed as such in the composition of the present invention. Alternatively, it may be further degraded, if necessary, by acid degradation, alkali degradation, enzymatic degradation, ultrasonication, etc. and the degradation product thus obtained may be employed in the composition of the present invention.

The succinoglucan content in the composition of the present invention preferably ranges from 0.01 to 15.0% by weight based on the total weight of the composition. When the succinoglucan content falls within a range of 0.1 to 10.0% by weight based on the total weight of the composition, in particular, the composition of the present invention is in the form of a gel showing a further improved long-term stability.

The succinoglucan content less than 0.01% by weight based on the total weight of the composition is not preferable, because the composition has only a poor long-term stability in this case. It is not preferable too that the content thereof exceeds 15.0% by weight, since the composition becomes sticky and gives an unfavorable feeling upon use in this case.

The water-swelling clay mineral to be used in the composition of the present invention is not particularly restricted, so long as it is a clay mineral capable of swelling in water. Either a natural one or a synthetic one having an arbitrary composition is usable therefor.

Examples of the water-swelling clay mineral include smectites such as montmorillonite, saponite, hectorite, beidellite, nontronite, sauconite and stevensite; and swelling micas.

The composition of the present invention may comprise either one of these water-swelling clay minerals or a combination of two or more of the same.

The water-swelling clay mineral content in the composition of the present invention preferably ranges from 0.01 to 15.0% by weight based on the total weight of the composition, still preferably from 0.1 to 10.0% by weight based on the total weight of the composition. When the content of the water-swelling clay mineral is less than 0.01% by weight based on the total weight of the composition, the obtained composition shows only a poor long-term stability. The content of the water-swelling clay mineral exceeding 15.0% by weight is not preferable, because the composition having the characteristics according to the present invention can be hardly obtained.

The composition of the present invention may further comprises cosmetically and/or pharmaceutically acceptable carriers, diluents, excipients, etc.

In addition to the succinoglucan and the water-swelling clay mineral, it is preferable that the composition of the present invention comprises an oily component. Addition of the oily component imparts to the composition a very excellent spreadability on the skin, much improved moist feel, etc., thereby giving a product having a more favorable feeling upon use as, in particular, cosmetics.

The oily component to be used in the composition of the present invention is not particularly restricted, so long as it is usable in compositions for external use such as cosmetics. Either a liquid component or a solid one may be used therefor. Examples of the oily component include liquid oils such as avocado oil, camellia oil, turtle oil, macadamia nut oil, corn oil, mink oil, olive oil, rapeseed oil, yolk oil, sesame oil, persic oil, wheat germ oil, sasanqua oil, castor oil, linseed oil, safflower oil, cotton seed oil, perilla oil, soybean oil, peanut oil, tea seed oil, torreya oil, rice bran oil, Chinese tung oil, Japanese tung oil, jojoba oil, germ oil, glyceryl trioctanoate, glyceryl triisopalmitate, cetyl isooctanoate, isopropyl myristate, liquid paraffin, squalane, isoparaffin, methyl silicone, methylphenyl silicone, oleyl alcohol and 2-octyldodecanol; and solid fats and waxes such as cacao fat, coconut oil, equine tallow, hardened coconut oil, palm oil, beef tallow, sheep tallow, hardened beef tallow, palm kernel oil, lard, beef bone fat, Japan wax kernel oil, hardened oil, beef foot tallow, Japan wax, hardened castor oil, beeswax, candelilla wax, cotton wax, carnauba wax, bayberry wax, insect wax, spermaceti, montan wax, rice bran wax, lanolin, kapok oil, lanolin acetate, liquid lanolin, sugar corn wax, isopropyl lanolin fatty acid, hexyl laurate, reduced lanolin, jojoba wax, hard lanolin, shellac wax, cholesterol, phytosterol, microcrystalline wax, behenyl alcohol, stearyl alcohol, cetyl alcohol, behenic acid, stearic acid and myristic acid.

The composition of the present invention may comprise either one of these oily components or a combination of two or more of the same.

The oily component content in the composition of the present invention preferably ranges from 0.1 to 40.0% by weight based on the total weight of the composition, still preferably from 0.3 to 30.0% by weight based on the total weight of the composition. It is unfavorable that the content of the oily component is less than 0.1% by weight based on the total weight of the composition, since the spreadability of the composition on the skin cannot be improved in this case. It is also unfavorable that the content thereof exceeds 40.0% by weight, since the composition exhibits a poor feeling upon use due to the deterioration in the refreshing feel in this case.

It is preferable that the composition of the present invention further comprises a surfactant. Addition of the surfactant can further improve the long-term stability of the composition of the present invention. When the composition of the present invention comprises an oily component, the long-term stability thereof may sometimes be deteriorated. In such a case, it is preferable to add a surfactant to the composition of the present invention so as to achieve a high long-term stability.

The surfactant to be used in the composition of the present invention is not particularly restricted, so long as it is a surfactant usable in compositions for external use such as cosmetics. Either nonionic, anionic, cationic or amphoteric surfactants may be employed. Examples thereof include sorbitan fatty acid esters, glycerol or polyglycerol fatty acid esters, propylene glycol fatty acid esters, polyoxyethylene (hereinafter referred to simply as POE) sorbitan fatty acid esters, POE sorbitol fatty acid esters, POE glycerol fatty acid esters, POE fatty acid esters, POE alkyl ethers, POE alkylphenyl ethers, POE/polyoxypropylene (hereinafter referred to simply as POP) alkyl ethers, POE castor oil or hardened castor oil derivatives, POE beeswax lanolin derivatives, alkanolamides, POE propylene glycol fatty acid esters, POE alkylamines, POE fatty acid amides, sucrose fatty acid esters, polyether-denatured silicone, fatty acid soaps, higher alkyl sulfate salts, alkyl ether sulfate salts, N-acylsarcosinate, higher fatty acid amidosulfonates, phosphate salts, sulfosuccinates, alkylbenzenesulfonates, N-acylglutamates, alkyltrimethylammonium salts, dialkyldimethylammonium salts, imidazoline-type amphoteric surfactants and betaine-type surfactants.

The composition of the present invention may comprise one of these surfactants or a combination of two or more of the same.

The content of the surfactant in the composition of the present invention may be appropriately determined so as not to deteriorate the feeling upon use and the safety of the product. It is preferable that the content thereof ranges from 0.01% to 5.0% by weight based on the total weight of the composition, still preferably from 0.05 to 2.0% by weight based on the total weight of the composition. It is not preferable that the content of the surfactant is less than 0.01% by weight based on the total weight of the composition, since the effect of improving the long-term stability cannot be satisfactorily achieved in this case. It is also unfavorable that the content thereof exceeds 5.0% by weight, since the feel of the composition in using is deteriorated in this case.

It is preferable that the composition of the present invention further comprises an alkyl acrylate.methacrylate copolymer. Addition of the alkyl acrylate.methacrylate copolymer can further improve the long-term stability of the composition. When the composition of the present invention comprises an oily component, the long-term stability thereof may sometimes be deteriorated. In such a case, it is particularly preferable to add an alkyl acrylate.methacrylate copolymer to the composition of the present invention so as to achieve a good long-term stability.

The alkyl acrylate.methacrylate copolymer to be used in the composition of the present invention is not particularly restricted, so long as it is an alkyl acrylate.methacrylate copolymer usable in compositions for external use such as cosmetics. That is to say, it is restricted neither in alkyl group nor in the degree of polymerization. For example, use may be made therefor of PEMULEN TR-2 (manufactured by BF GOODRICH).

The content of the alkyl acrylate.methacrylate copolymer in the composition of the present invention may be appropriately determined so as not to deteriorate the feeling upon use and the safety of the product. It is preferable that the content thereof ranges from 0.005 to 5.0% by weight based on the total weight of the composition, still preferably from 0.01 to 2.0% by weight based on the total weight of the composition. It is not preferable that the content of the alkyl acrylate.methacrylate copolymer is less than 0.005% by weight based on the total weight of the composition, since the effect of improving the long-term stability cannot be satisfactorily achieved in this case. It is also unfavorable that the content thereof exceeds 5.0% by weight, since the feel of the composition in using is deteriorated in this case.

In addition to the components as described above, the composition of the present invention may comprise components commonly employed in the art, so long as the effects of the present invention are not worsened thereby. Examples of such components are as follows:

glycols such as propylene glycol, dipropylene glycol, 1,3-butylene glycol, 1,4-butylene glycol, diethylene glycol, triethylene glycol and glycols having higher molecular weight;

glycerol, diglycerol, triglycerol and polyglycerols having higher molecular weight;

sugar alcohols such as sorbitol, mannitol, maltitol, xylitol and erythritol;

saccharides such as fructose, glucose, galactose, maltose, lactose and trehalose;

inorganic powders such as talc, kaolin, mica, sericite, muscovite, phlogopite, synthetic mica, lepidolite, biotite, lithia mica, vermiculite, magnesium carbonate, calcium carbonate, aluminum silicate, barium silicate, calcium silicate, magnesium silicate, strontium silicate, metal tungstate, magnesium, silica, zeolite, barium sulfate, calcined calcium sulfate (calcined gypsum), calcium phosphate, fluorine apatite, hydroxyapatite, ceramic powder, metal soaps (zinc myristate, calcium palmitate, aluminum stearate, etc.) and boron nitride;

organic powders such as polyamide resin powder (nylon powder), polyethylene powder, poly(methyl methacrylate) powder, polystyrene powder, styrene/acrylic acid copolymer powder, benzoguanamine resin powder, poly(ethylene tetrafluoride) powder and cellulose powder;

inorganic white pigments such as titanium dioxide and zinc oxide; inorganic red pigments such as iron oxide (red iron oxide) and iron titanate; inorganic brown pigments such as γ-iron oxide; inorganic yellow pigments such as yellow iron oxide and yellow ocher; inorganic black pigments such as black iron oxide, carbon black and low-dimensional titanium oxide; inorganic purple pigments such as manganese violet and cobalt violet; inorganic green pigments such as chromium oxide, chromium hydroxide and cobalt titanate; inorganic blue pigments such as ultramarine and Prussian blue; pearl pigments such as titanium oxide-coated mica, titanium oxide-coated bismuth oxychloride, titanium oxide-coated talc, colored titanium oxide-coated mica, bismuth oxychloride and fish scale; metal powder pigments such as aluminum powder and copper powder; organic pigments such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401 and Blue No. 404; organic pigments containing zirconium, barium or aluminum lakes such as Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3 and Blue No. 1; natural colorants such as chlorophyll and β-carotene;

vegetable polymers such as acacia, tragacanth gum, galactan, guar gum, carob gum, karaya gum, gellan gum and carrageenan; microbial polymers such as xanthan gum, dextran, and pullulan; animal polymers such as collagen, casein, albumin and gelatin; starch polymers such as carboxymethyl starch and methylhydroxypropyl starch; cellulose polymers such as methyl cellulose, ethyl cellulose, methylhydroxypropyl cellulose, hydroxyethyl cellulose, cellulose sodium sulfate, hydroxypropyl cellulose, carboxymethyl cellulose sodium and crystalline cellulose; alginic acid polymers such as sodium alginate and propyelne glycol alginate; vinyl polymers such as polyvinyl alcohol, polyvinyl acetate, polyvinyl methyl ether, polyvinylpyrrolidone, vinylpyrrolidone/vinyl acetate copolymer and carboxyvinyl polymer; acrylic polymers such as sodium polyacrylate, polyethyl acrylate, polyacrylic alkanolamine, alkyl methacrylate/diemthylaminoethyl methacrylate copolymer, poly (2-acrylmido-2-methylpropanesulfonic acid) and polymethacryloyloxytrimethylammonium;

agents such as ultraviolet absorbers, chelating agents, vitamins, bactericides, anti-inflammatory agents, preservatives, plant extracts and refrigerants; and lower alcohols such as ethanol and isopropyl alcohol.

The composition of the present invention can be applied to the skin, hair, etc. The composition of the present invention may be in various forms including aqueous solution systems, solubilized systems, emulsion systems, oily liquid systems, gel systems, ointment systems, aerosols, water/oil two-layered systems and water/oil/powder three-layered systems. Although the composition of the present invention is particularly useful as cosmetics, it is also usable as pharmaceuticals, quasi pharmaceuticals, etc. When the composition of the present invention is to be used as fundamental cosmetics, it may be processed into skin-care essences (cosmetic lotions), milky lotions, creams, gels, etc. When the composition of the present invention is to be used as makeup cosmetics, it may be processed into foundations, eyeshadows, mascaras, cosmetic bases, etc. When the composition of the present invention is to be used as hair-care products, it may be processed into hair growth stimulants, hair styling agents, etc. When the composition of the present invention is to be used as body-care products, it may be processed into sunscreens, suntans, after sun care products, hand creams, etc. When the composition of the present invention is to be used as pharmaceuticals or quasi pharmaceuticals, it may be processed into various ointments, etc. However, the composition of the present invention is not restricted to these dosage forms or product forms.

The present invention will be described in greater detail by reference to the following Examples, but it should be understood that the invention is not construed as being limited thereto.

REFERENCE EXAMPLE 1

Example of the Production of Succinoglucan

Succinoglucan was produced in accordance with a method described in JP-B-6-74283 (the term "JP-B" as used herein means an "examined Japanese patent publication"). Namely, fermentation was performed by using *Agrobacterium tumefaciens* I-736 strain in the culture medium having the composition as will be specified hereinafter.

More particularly speaking, the culture medium was inoculated with the *Agrobacterium tumefaciens* I-736 strain which was then cultured in a 20 L (15 L available) Biolaffite™ container at 28° C. under agitation at 400 rpm with the use of a Ruston™ agitator while aerating at a rate of 825 L/h. After performing the culture under agitation for 90 hours (i.e., the time required for completely or substantially completely consuming sucrose), 66% by weight, based on the weight of the sucrose employed, of hetero-polysaccharides were obtained. When measured with a Brookfield LTV™ viscometer by using a cylindrical spindle No. 4 at 30 rpm, the fermented liquor had a viscosity of 6800 Pa/s.

After heating the fermented liquor as described above at 90° C. for 3 minutes, 2 kg of succinoglucan was recovered therefrom in the following manner. Namely, 2300 mL of isopropyl alcohol was added, after heating, to the fermented liquor. Next, 150 g of sodium sulfate was further added thereto to form a precipitate. Fibers formed from the precipitate were dehydrated with 1200 mL portions of isopropyl alcohol twice. Next, the dehydrated fibers were disintegrated under elevated pressure and dried in an oven at 85° C. The dried matter thus obtained was ground to thereby give succinoglucan as a yellowish white powder.

The succinoglucan thus obtained was employed in the subsequent Examples.

Composition of Culture Medium:

| Component | Content (wt. %) |
|---|---|
| CSL (corn steep liquor) | 11.0 |
| K$_2$HPO$_4$ | 4.0 |
| MgSO$_4$•7H$_2$O | 0.5 |
| Sucrose | 25.0 |
| Purified water | the balance |

Next, examples of the formulation of the composition of the present invention will be illustrated. However, it is to be understood that the technical scope of the present invention is not restricted thereto.

Unless otherwise noted, contents will be given in these Examples in % by weight based on the whole system in which the corresponding components are contained.

In these Examples, the feeling upon use and the long-term stability of the composition of the present invention were evaluated based on the following criteria Feeling Upon Use Feeling upon use (spreadability at application, moist feel after using and refreshing feel after using) was evaluated by 20 female panels in accordance with the following criteria.

⊚: evaluated as good by 16 or more panelists.
○: evaluated as good by 10 to 15 panelists.
Δ: evaluated as good by 6 to 9 panelists.
X: evaluated as good by 5 or less panelists.

Long-term Stability

A temperature test was effected at 0° C., room temperature, 37° C. and 50° C. and the results were evaluated in accordance with the following criteria.

⊚: no abnormality (separation, etc.) observed at every test temperature.
○: slight abnormality (separation, etc.) observed after storing at 50° C. for 1 month.
Δ: slight abnormality (separation, etc.) observed after storing at 37° C. for 1 month.
X: abnormality (separation, etc.) observed after storing at 0° C. or room temperature for 1 month.

EXAMPLES 1 TO 7

Cream:

Table 1 summarizes the components and compositions of the creams of Examples 1 to 7 and the result of the evaluation of the feeling upon use and the long-term stability thereof.

TABLE 1

| | Ex. 1 | Ex. 2 | Ex. 3 | Ex. 4 | Ex. 5 | Ex. 6 | Ex. 7 |
|---|---|---|---|---|---|---|---|
| | Component (wt. %) | | | | | | |
| A. water-swelling clay mineral phase | | | | | | | |
| deionized water | 30.0 | 30.0 | 30.0 | 30.0 | 30.0 | 30.0 | 30.0 |
| dipropylene glycol | 5.0 | 5.0 | 5.0 | 5.0 | 5.0 | 5.0 | 5.0 |
| saponite (SUMECTON™ SA mfd. by Kunimine Kogyo) | 3.0 | 3.0 | 3.0 | 3.0 | 3.0 | 3.0 | 3.0 |
| B. succinoglucan phase | | | | | | | |
| deionized water | 56.892 | 56.88 | 56.7 | 54.9 | 48.9 | 43.9 | 39.9 |
| ethanol | 5.0 | 5.0 | 5.0 | 5.0 | 5.0 | 5.0 | 5.0 |
| methyl paraben | 0.1 | 0.1 | 0.1 | 0.1 | 0.1 | 0.1 | 0.1 |
| succinoglucan | 0.008 | 0.02 | 0.2 | 2.0 | 8.0 | 13.0 | 17.0 |
| | Result of evaluation | | | | | | |
| spreadability at application | ○ | ○ | ○ | ○ | ○ | ○ | ○ |
| moist feel after using | ○ | ○ | ○ | ○ | ○ | ○ | ○ |
| refreshing feel after using | ⊚ | ⊚ | ⊚ | ⊚ | ⊚ | ○ | ⊚ |
| long-term stability | Δ | ○ | ⊚ | ⊚ | ⊚ | ⊚ | Δ |

Production Process

The water-swelling clay mineral phase A was homogeneously swollen in a homodisperser. Then the succinoglucan phase B, which had been dissolved by stirring in another pot, was added thereto and the resulting mixture was homogeneously mixed by stirring, thus giving a cream.

As is clear from the result in Table 1, the cream obtained by using less than 0.01% by weight of the succinoglucan was unfavorable because it gave a good feeling upon use but showed a poor long-term stability. When the succinoglucan content exceeded 0.1% by weight, the obtained creams were in the form of a gel and showed very excellent long-term stability. When the succinoglucan content exceeded 15.0% by weight, the obtained cream was unfavorable since it imparted a sticky feeling upon use and failed to give any refreshing feel after using.

As supported by the result shown in Table 1, the succinoglucan content in the composition of the present invention preferably ranges from 0.01 to 15.0% by weight, still preferably from 0.1 to 10.0% by weight.

EXAMPLE 8 TO 13 AND COMPARATIVE EXAMPLE 1

Whitening Cream:

Table 2 summarizes the components and compositions of the whitening creams of Examples 8 to 13 and Comparative Example 1 and the result of the evaluation of the feeling upon use and the long-term stability thereof.

Production Process

The water-swelling clay mineral phase A was homogeneously swollen in a homodisperser. Then the succinoglucan phase B, which had been dissolved by stirring in another pot, was added thereto and the resulting mixture was homogeneously mixed by stirring, thus giving a whitening cream.

When carboxyvinyl polymer was used as a substitute for succinoglucan, the obtained creams were poor in long-term stability (Example 11, Comparative Example 1).

As the result in Table 2 clearly shows, the whitening cream obtained by using less than 0.01% by weight of the water-swelling clay mineral was unfavorable, since it showed a poor long-term stability. When the water-swelling clay mineral content exceeded 15.0% by weight, it became difficult to produce a whitening cream having the characteristics of the present invention.

As supported by the result shown in Table 2, the water-swelling clay mineral content in the composition of the present invention preferably ranges from 0.01 to 15.0% by weight, still preferably from 0.1 to 10.0% by weight.

EXAMPLES 14 TO 20 AND COMPARATIVE EXAMPLE 2

Essence:

Table 3 summarizes the components and compositions of the essences of Examples 14 to 20 and Comparative Example 2 and the result of the evaluation of the feeling upon use and the long-term stability thereof.

TABLE 2

|  | Ex. 8 | Ex. 9 | Ex. 10 | Ex. 11 | Ex. 12 | Ex. 13 | Comp. Ex. 1 |
|---|---|---|---|---|---|---|---|
| Component (wt. %) | | | | | | | |
| A. water-swelling clay mineral phase | | | | | | | |
| deionized water | 50.0 | 50.0 | 50.0 | 50.0 | 50.0 | 50.0 | 50.0 |
| glycerol | 5.0 | 5.0 | 5.0 | 5.0 | 5.0 | 5.0 | 5.0 |
| montmorillonite (KUNIPIA ™ G-4 mfd. by Kunimine Kogyo) | 0.008 | 0.02 | 2.0 | 6.0 | 10.0 | 13.0 | 6.0 |
| diglucoside ascorbate | 2.0 | 2.0 | 2.0 | 2.0 | 2.0 | 2.0 | 2.0 |
| B. succinoglucan phase | | | | | | | |
| deionized water | 38.892 | 38.88 | 36.9 | 32.9 | 28.9 | 25.9 | 32.9 |
| isopropyl alcohol | 3.0 | 3.0 | 3.0 | 3.0 | 3.0 | 3.0 | 3.0 |
| methyl paraben | 0.1 | 0.1 | 0.1 | 0.1 | 0.1 | 0.1 | 0.1 |
| succinoglucan | 1.0 | 1.0 | 1.0 | 1.0 | 1.0 | 1.0 | — |
| carboxyvinyl polymer | — | — | — | — | — | — | 1.0 |
| Result of evaluation | | | | | | | |
| spreadability at application | ○ | ○ | ○ | ○ | ○ | ○ | ○ |
| moist feel after using | ○ | ○ | ○ | ○ | ○ | ○ | ○ |
| refreshing feel after using | ⊚ | ⊚ | ⊚ | ⊚ | ⊚ | ○ | ○ |
| long-term stability | Δ | ○ | ⊚ | ⊚ | ⊚ | ⊚ | X |

TABLE 3

|  | Ex. 14 | Ex. 15 | Ex. 16 | Ex. 17 | Ex. 18 | Ex. 19 | Ex. 20 | Comp. Ex. 2 |
|---|---|---|---|---|---|---|---|---|
| Component (wt. %) | | | | | | | | |
| A. water-swelling clay mineral phase | | | | | | | | |
| deionized water | 15.0 | 15.0 | 15.0 | 15.0 | 15.0 | 15.0 | 15.0 | 15.0 |
| trehalose | 1.0 | 1.0 | 1.0 | 1.0 | 1.0 | 1.0 | 1.0 | 1.0 |

TABLE 3-continued

|  | Ex. 14 | Ex. 15 | Ex. 16 | Ex. 17 | Ex. 18 | Ex. 19 | Ex. 20 | Comp. Ex. 2 |
|---|---|---|---|---|---|---|---|---|
| arginine hydrochloride | 1.0 | 1.0 | 1.0 | 1.0 | 1.0 | 1.0 | 1.0 | 1.0 |
| saponite (SUMECTON ™ SA mfd. by Kunimine Kogyo) | 1.0 | 1.0 | 1.0 | 1.0 | 1.0 | 1.0 | 1.0 | 1.0 |
| B. succinoglucan phase | | | | | | | | |
| deionized water | 67.57 | 69.5 | 69.25 | 67.65 | 41.65 | 32.65 | 27.65 | 41.65 |
| ethanol | 5.0 | 5.0 | 5.0 | 5.0 | 5.0 | 5.0 | 5.0 | 5.0 |
| methyl paraben | 0.1 | 0.1 | 0.1 | 0.1 | 0.1 | 0.1 | 0.1 | 0.1 |
| succinoglucan | 0.2 | 0.2 | 0.2 | 0.2 | 0.2 | 0.2 | 0.2 | — |
| xanthan gum | — | — | — | — | — | — | — | 0.2 |
| C. oily component phase | | | | | | | | |
| 1,3-butylene glycol | 5.0 | 5.0 | 5.0 | 5.0 | 5.0 | 5.0 | 5.0 | 5.0 |
| POE (60 mol) hardened castor oil | 2.0 | 2.0 | 2.0 | 2.0 | 2.0 | 2.0 | 2.0 | 2.0 |
| squalane | 0.08 | 0.15 | 0.4 | 2.0 | 28.0 | 37.0 | 42.0 | 28.0 |
| tocopherol acetate | 0.05 | 0.05 | 0.05 | 0.05 | 0.05 | 0.05 | 0.05 | 0.05 |
| Result of evaluation | | | | | | | | |
| spreadability at application | ◯ | ◎ | ◎ | ◎ | ◎ | ◎ | ◎ | Δ |
| moist feel after using | ◯ | ◯ | ◎ | ◎ | ◎ | ◎ | ◎ | Δ |
| refreshing feel after using | ◎ | ◎ | ◎ | ◎ | ◎ | ◯ | Δ | X |
| long-term stability | ◎ | ◎ | ◎ | ◎ | ◎ | ◎ | ◎ | ◯ |

Production Process

The water-swelling clay mineral phase A was homogeneously swollen in a homodisperser. Then the succinoglucan phase B, which had been dissolved by stirring in another pot, was added thereto and the resulting mixture was homogeneously mixed by stirring. Further, the oily component phase C, which had been prepared in another pot by using a homomixer, was added thereto and the resulting mixture was homogeneously mixed by stirring, thus giving an essence.

When xanthan gum was used as a substitute for succinoglucan, the obtained essences were poor in the feeling upon use, in particular, the refreshing feel after using (Example 18, Comparative Example 2).

As the result given in Table 3 clearly show, the spreadability at application and the moist feel after using of the composition of the present invention were improved by adding squalane (i.e., an oily component) thereto. When the squalane content was less than 0.1% by weight, however, the spreadability at application and the moist feel after using of the composition could not be sufficiently improved. On the other hand, it is unfavorable that the squalane content exceeded 40.0% by weight, since the refreshing feel after using was lost and the feeling upon use was worsened in this case.

As supported by the result given in Table 3, the oily component content in the composition of the present invention preferably ranges from 0.1 to 40.0% by weight, still preferably from 0.3 to 30.0% by weight.

EXAMPLES 21 TO 25

Cosmetic Base:

Table 4 summarizes the components and compositions of the cosmetic bases of Examples 21 to 25 and the result of the evaluation of the feeling upon use and the long-term stability thereof.

TABLE 4

|  | Ex. 21 | Ex. 22 | Ex. 23 | Ex. 24 | Ex. 25 |
|---|---|---|---|---|---|
| Component (wt. %) | | | | | |
| A. water-swelling clay mineral phase | | | | | |
| deionized water | 15.0 | 15.0 | 15.0 | 15.0 | 15.0 |
| xylitol | 1.0 | 1.0 | 1.0 | 1.0 | 1.0 |
| *Saxifraga stolonifera* extract | 1.0 | 1.0 | 1.0 | 1.0 | 1.0 |
| saponite (VEEGUM ™ S-6198 mfd. by R T. Vanderbilt) | 2.0 | 2.0 | 2.0 | 2.0 | 2.0 |
| citric acid | 0.1 | 0.1 | 0.1 | 0.1 | 0.1 |
| sodium citrate | 0.1 | 0.1 | 0.1 | 0.1 | 0.1 |
| B. succinoglucan phase | | | | | |
| deionized water | 57.16 | 57.15 | 57.06 | 56.16 | 54.16 |
| ethanol | 15.0 | 15.0 | 15.0 | 15.0 | 15.0 |
| methyl paraben | 0.1 | 0.1 | 0.1 | 0.1 | 0.1 |
| succinoglucan | 0.5 | 0.5 | 0.5 | 0.5 | 0.5 |
| trisodium edetate | 0.02 | 0.02 | 0.02 | 0.02 | 0.02 |
| C. oily component phase | | | | | |
| POE (60 mol) hardened castor oil | — | 0.01 | 0.1 | 1.0 | 3.0 |
| dimethyl polysiloxane (6 cs) | 3.0 | 3.0 | 3.0 | 3.0 | 3.0 |
| decamethyl cyclopentasiloxane | 5.0 | 5.0 | 5.0 | 5.0 | 5.0 |
| vitamin A palmitate | 0.02 | 0.02 | 0.02 | 0.02 | 0.02 |
| Result of evaluation | | | | | |
| spreadability at application | ◎ | ◎ | ◎ | ◎ | ◎ |
| moist feel after using | ◎ | ◎ | ◎ | ◎ | ◎ |
| refreshing feel after using | ◎ | ◎ | ◎ | ◎ | ◯ |
| long-term stability | Δ | ◯ | ◎ | ◎ | ◎ |

Production Process

The water-swelling clay mineral phase A was homogeneously swollen in a homodisperser. Then the succinoglucan phase B, which had been dissolved by stirring in another pot, was added thereto and the resulting mixture was homogeneously mixed by stirring. Further, the oily component phase C, which had been-prepared in another pot by using a homomixer, was added thereto and the resulting mixture was homogeneously mixed by stirring, thus giving a cosmetic base.

As the result given in Table 4 clearly show, the long-term stability of the cosmetic bases was somewhat deteriorated by using dimethyl polysiloxane (6 cs) and decamethyl cyclopentasiloxane (i.e., oily components) in addition to the water-swelling clay mineral and succinoglucan. However, cosmetic bases having excellent long-term stability could be obtained by further adding 0.01% by weight or more, in particular, 0.1% by weight or more, of a surfactant.

EXAMPLES 26 to 29

Cosmetic Base:

Table 5 summarizes the components and compositions of the cosmetic bases of Example 21 and Examples 26 to 29 and the result of the evaluation of the feeling upon use and the long-term stability thereof.

TABLE 5

|  | Ex. 21 | Ex. 26 | Ex. 27 | Ex. 28 | Ex. 29 |
|---|---|---|---|---|---|
| Component (wt. %) | | | | | |
| A. water-swelling clay mineral phase | | | | | |
| deionized water | 15.0 | 15.0 | 15.0 | 15.0 | 15.0 |
| xylitol | 1.0 | 1.0 | 1.0 | 1.0 | 1.0 |
| *Saxifraga stolonifera* extract | 1.0 | 1.0 | 1.0 | 1.0 | 1.0 |
| saponite (VEEGUM ™ S-6198 mfd. by R T. Vanderbilt) | 2.0 | 2.0 | 2.0 | 2.0 | 2.0 |
| citric acid | 0.1 | 0.1 | 0.1 | 0.1 | 0.1 |
| sodium citrate | 0.1 | 0.1 | 0.1 | 0.1 | 0.1 |
| B. succinoglucan phase | | | | | |
| deionized water | 57.16 | 57.155 | 57.11 | 56.66 | 55.16 |
| ethanol | 15.0 | 15.0 | 15.0 | 15.0 | 15.0 |
| methyl paraben | 0.1 | 0.1 | 0.1 | 0.1 | 0.1 |
| succinoglucan | 0.5 | 0.5 | 0.5 | 0.5 | 0.5 |
| trisodium edetate | 0.02 | 0.02 | 0.02 | 0.02 | 0.02 |
| C. oily component phase | | | | | |
| alkyl acrylate•methacrylate copolymer (PEMULEN ™ TR-2 mfd. by B F Goodrich) | — | 0.005 | 0.05 | 0.5 | 2.0 |
| dimethyl polysiloxane (6 cs) | 3.0 | 3.0 | 3.0 | 3.0 | 3.0 |
| decamethyl cyclopentasiloxane | 5.0 | 5.0 | 5.0 | 5.0 | 5.0 |
| vitamin A palmitate | 0.02 | 0.02 | 0.02 | 0.02 | 0.02 |
| Result of evaluation | | | | | |
| spreadability at application | ⊚ | ⊚ | ⊚ | ⊚ | ⊚ |
| moist feel after using | ⊚ | ⊚ | ⊚ | ⊚ | ⊚ |
| refreshing feel after using | ⊚ | ⊚ | ⊚ | ⊚ | ○ |
| long-term stability | Δ | ○ | ⊚ | ⊚ | ⊚ |

Production Process

The cosmetic bases of Examples 26 to 29 were produced as in Examples 21 to 25.

As the result given Table 5 clearly show, cosmetic bases giving an excellent moist feel after using and having a high long-term stability could be obtained by using 0.005% by weight or more, in particular, 0.05% by weight or more, of the alkyl acrylate.methacrylate copolymer in addition to the water-swelling clay mineral, succinoglucan and the oily component.

EXAMPLE 30

Foundation:

Table 6 shows the components and composition of the foundation of Example 30 and the result of the evaluation of the feeling upon use and the long-term stability thereof.

TABLE 6

|  | Example 30 (wt. %) |
|---|---|
| Component | |
| A. water-swelling clay mineral phase | |
| deionized water | 25.0 |
| erythritol | 1.0 |
| polyethylene glycol 1000 | 3.0 |
| hectorite (LOPONITE ™ mfd. by Laporte Industries) | 3.0 |
| lactic acid | 0.1 |
| sodium lactate | 0.05 |
| B. succinoglucan phase | |
| deionized water | 24.55 |
| ethanol | 3.0 |
| methyl paraben | 0.1 |
| phenoxyethanol | 0.2 |
| succinoglucan | 0.4 |
| C. oily component phase | |
| POE (20 mol) behenyl ether | 0.5 |
| macadamia nut oil | 2.0 |
| decamethyl cyclopentasiloxane | 2.0 |
| D. powder phase | |
| deionized water | 20.0 |
| sodium metaphosphate | 0.03 |
| titanium dioxide | 4.0 |
| mica | 10.0 |
| iron oxide (red) | 0.02 |
| iron oxide (yellow) | 0.04 |
| iron oxide (black) | 0.01 |
| silicone powder | 1.0 |
| Result of evaluation | |
| spreadability at application | ⊚ |
| moist feel after using | ⊚ |
| refreshing feel after using | ⊚ |
| long-term stability | ⊚ |

Production Process

The water-swelling clay mineral phase A was homogeneously swollen in a homodisperser. Then the succinoglucan phase B, which had been dissolved by stirring in another pot, was added thereto and the resulting mixture was homogeneously mixed by stirring. Further, the oily component phase C, which had been prepared in another pot by using a homomixer, was added thereto and the resulting mixture was homogeneously mixed by stirring. Furthermore, the powder phase D, which had been prepared in another pot by using a homomixer, was added thereto and the resulting mixture was homogeneously mixed by stirring, thus giving a foundation.

As the result given in Table 6 clearly show, the foundation according to the present invention was excellent in the feeling upon use and the long-term stability.

EXAMPLE 31

Sunscreen:

Table 7 shows the components and composition of the sunscreen of Example 31 and the result of the evaluation of the feeling upon use and the long-term stability thereof.

TABLE 7

| Component | Example 31 (wt. %) |
|---|---|
| A. water-swelling clay mineral phase | |
| deionized water | 20.0 |
| dipropylene glycol | 3.0 |
| montmorillonite (KUNIPIA ™ mfd. by Kunimine Kogyo) | 2.0 |
| B. succinoglucan phase | |
| deionized water | 22.17 |
| ethanol | 10.0 |
| methyl paraben | 0.1 |
| phenoxyethanol | 0.2 |
| succinoglucan | 0.5 |
| C. oily component phase | |
| POE (30 mol) stearate | 0.5 |
| calcium stearate | 0.5 |
| methyl polysiloxane with high degree of polymerization (2)-methyl polysiloxane solution (20%) | 2.0 |
| decamethyl cyclopentasiloxane | 2.0 |
| octamethoxy cinnamate | 5.0 |
| D. powder phase | |
| deionized water | 20.0 |
| sodium metaphosphate | 0.03 |
| titanium dioxide | 6.0 |
| zinc oxide | 5.0 |
| silica | 1.0 |
| Result of evaluation | |
| spreadability at application | ⊚ |
| moist feel after using | ⊚ |
| refreshing feel after using | ⊚ |
| long-term stability | ⊚ |

Production Process

The water-swelling clay mineral phase A was homogeneously swollen in a homodisperser. Then the succinoglucan phase B, which had been dissolved by stirring in another pot, was added thereto and the resulting mixture was homogeneously mixed by stirring. Further, the oily component phase C, which had been prepared in another pot by using a homomixer, was added thereto and the resulting mixture was homogeneously mixed by stirring. Furthermore, the powder phase D, which had been prepared in another pot by using a homomixer, was added thereto and the resulting mixture was homogeneously mixed by stirring, thus giving a sunscreen.

The result given in Table 7 shows that the sunscreen according to the present invention is excellent in the feeling upon use and the long-term stability.

EXAMPLE 32

Milky Lotion:

Table 8 shows the components and composition of the milky lotion of Example 32 and the result of the evaluation of the feeling upon use and the long-term stability thereof.

TABLE 8

| Component | Example 32 (wt. %) |
|---|---|
| A. water-swelling clay mineral phase | |
| deionized water | 15.0 |
| 1,3-butylene glycol | 3.0 |
| glycerol | 5.0 |
| montmorillonite (KUNIPIA ™ mfd. by Kunimine Kogyo) | 0.5 |
| B. succinoglucan phase | |
| deionized water | 61.45 |
| ethanol | 5.0 |
| methyl paraben | 0.1 |
| phenoxy ethanol | 2.0 |
| succinoglucan | 0.2 |
| xanthan gum | 0.4 |
| trisodium edetate | 0.05 |
|  | 0.05 |
| C. oily component phase | |
| alkyl acrylate•methacrylate copolymer (PEMULEN ™ TR-2, mfd. by B F Goodrich) | 0.1 |
| dimethyl polysiloxane (6 cs) | 2.0 |
| jojoba oil | 5.0 |
| octamethoxy cinnamate | 0.1 |
| perfume | 0.05 |
| Result of evaluation | |
| spreadability at application | ⊚ |
| moist feel after using | ⊚ |
| refreshing feel after using | ⊚ |
| long-term stability | ⊚ |

Production Process

The water-swelling clay mineral phase A was homogeneously swollen in a homodisperser. Then the succinoglucan phase B, which had been dissolved by stirring in another pot, was added thereto and the resulting mixture was homogeneously mixed by stirring. Further, the oily component phase C, which had been prepared in another pot by using a homomixer, was added thereto and the resulting mixture was homogeneously mixed by stirring, thus giving a milky lotion.

As the results given in Table 8 clearly show, the milky lotion according to the present invention is excellent in the feeling upon use and the long-term stability. The present invention provides a composition for external use which is useful particularly as cosmetics giving a novel feeling upon use, satisfying the diversified requirements by consumers and being excellent in long-term stability.

While the invention has been described in detail and with reference to specific embodiments thereof, it will be apparent to one skilled in the art that various changes and modifications can be made therein without departing from the spirit and scope thereof.

This application is based on Japanese patent applications No. Hei.-10-284784 filed on Sep. 21, 1998 and No. Hei.-11-221118 filed on Aug. 4, 1999, incorporated herein by reference.

What is claimed is:

1. A method for increasing moisturizing effect of a cosmetic composition selected from the group consisting of skin care, body care or make up for topical administration to skin comprising combining succinoglucan which is 0.01 to 15.0%, a water-swelling clay mineral which is 0.01 to 15.0%, an oily component which is 0.1 to 40.0%, and alkyl acrylate•methacrylate copolymer which is 0.005 to 5.0% to provide said cosmetic composition, wherein all percentages are by weight based upon the total weight of the composition.

2. A method for increasing spreadability of a cosmetic composition selected from the group consisting of skin care, body care or make up for topical administration to skin comprising combining succinoglucan which is 0.01 to 15.0%, a water-swelling clay mineral which is 0.01 to 15.0%, an oily component which is 0.1 to 40.0%, and alkyl acrylate.methacrylate copolymer which is 0.005 to 5.0% to provide said cosmetic composition, wherein all percentages are by weight based upon the total weight of the composition.

3. A method for increasing long-term stability of a cosmetic composition selected from the group consisting of skin care, body care or make up for topical administration to skin comprising combining succinoglucan which is 0.01 to 15.0%, a water-swelling clay mineral which is 0.01 to 15.0%, an oily component which is 0.1 to 40.0%, and alkyl acrylate.methacrylate copolymer which is 0.005 to 5.0% to provide said cosmetic composition, wherein all percentages are by weight based upon the total weight of the composition.

4. A method for increasing refreshing feel after using a cosmetic composition selected from the group consisting of skin care, body care or make up for topical administration to skin comprising combining succinoglucan which is 0.01 to 15.0%, and a water-swelling clay mineral which is 0.01 to 15.0%, an oily component which is 0.1 to 40.0%, and alkyl acrylate.methacrylate copolymer which is 0.005 to 5.0% to provide said cosmetic composition, wherein all percentages are by weight based upon the total weight of the composition.

5. The method of claim 1, wherein said composition comprises an amount of surfactant which is from 0.01 to 5.0 by weight based on the total weight of the composition.

6. The method of claim 1, wherein said composition further comprises a carrier for external application to skin.

7. The method of claim 2, wherein said composition comprises an amount of surfactant which is from 0.01 to 5.0 by weight based on the total weight of the composition.

8. The method of claim 2, wherein said composition further comprises a carrier for external application to skin.

9. The method of claim 3, wherein said composition comprises an amount of surfactant which is from 0.01 to 5.0 by weight based on the total weight of the composition.

10. The method of claim 3, wherein said composition further comprises a carrier for external application to skin.

11. The method of claim 4, wherein said composition comprises an amount of surfactant which is from 0.01 to 5.0 by weight based on the total weight of the composition.

12. The method of claim 4, wherein said composition further comprises a carrier for external application to skin.

* * * * *